United States Patent [19]

Robin et al.

[11] Patent Number: 4,900,842
[45] Date of Patent: Feb. 13, 1990

[54] ORGANIC COMPOUNDS OF THE TETRATHIAFLUVALENE TYPE WHICH CAN BE USED TO MAKE LANGMUIR-BLODGETT CONDUCTING FILMS AND METHOD FOR THEIR MANUFACTURE

[75] Inventors: Philippe Robin, Le Plessis Robinson; Albert Robert, Rennes; Francoise Bertho, Mun de Bretagne; Patrick Batail, Paris, all of France

[73] Assignee: Thomson-CSF, Paris, France

[21] Appl. No.: 154,013

[22] Filed: Feb. 9, 1988

[30] Foreign Application Priority Data

Feb. 13, 1987 [FR] France ................................ 87 01869

[51] Int. Cl.$^4$ ........................................... C07D 339/06
[52] U.S. Cl. .......................................... 549/36; 549/37
[58] Field of Search ................................... 549/37, 36

[56] References Cited

U.S. PATENT DOCUMENTS 4,691,028 9/1987 Inokschi ................................. 549/36

OTHER PUBLICATIONS

Engler, E. M., *Syntesis of Tetrathifulvalene Derivatives via Polymer—Bound Triphenylphosphine,* Mar. 1987.
*Tetrahedron,* vol. 40, No. 10, 1984, pp. 1817–1821, A. Souizi et al.
*Zhurnal Obshchei Khimii,* vol. 56, No. 5, mai 1986, pp. 1157–1160, v. Yu., Khodorkovskii et al.

Primary Examiner—Mary C. Lee
Assistant Examiner—MarySue Howard
Attorney, Agent, or Firm—Oblon, Spivak, McClelland, Maier & Neudstadt

[57] ABSTRACT

The invention pertains to organic compounds of the tetrahiafulvalene type made amphiphillic by substitution of the radicals $R^1$ and $R^2$ meeting one of the following conditions:

$R^1$ is a hydrophilic group and $R^2$ is a hydrophobic group, $R^1$ is a hydrophobic group and $R^2$ is a hydrophilic group, $R^1$ is an aromatic group and $R^2$ is a group having a long carbon-containing chain with a hydrophobic nature and a hydrophilic end.

These organic compounds can form Langmuir-Blodgett films which are made anisotropically conductive by doping.

5 Claims, 2 Drawing Sheets

FIG_1
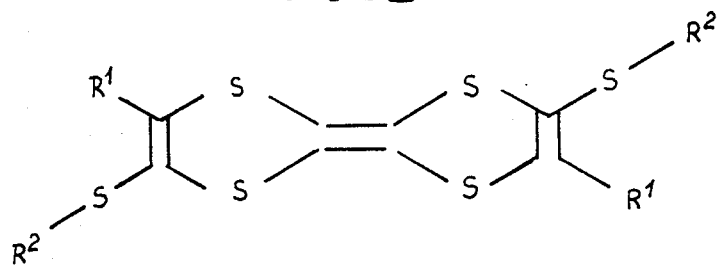
FIG_2
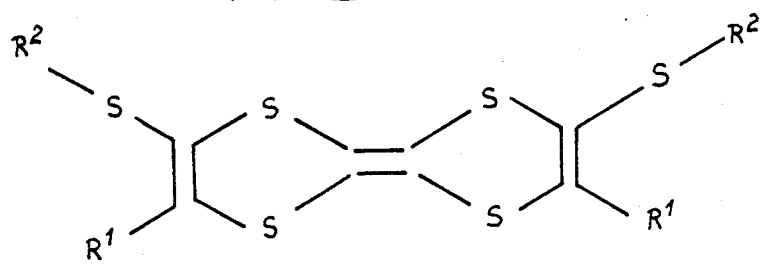
FIG_4
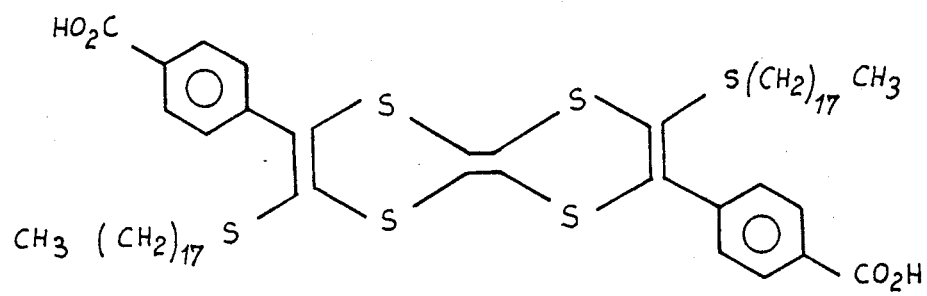

FIG_3
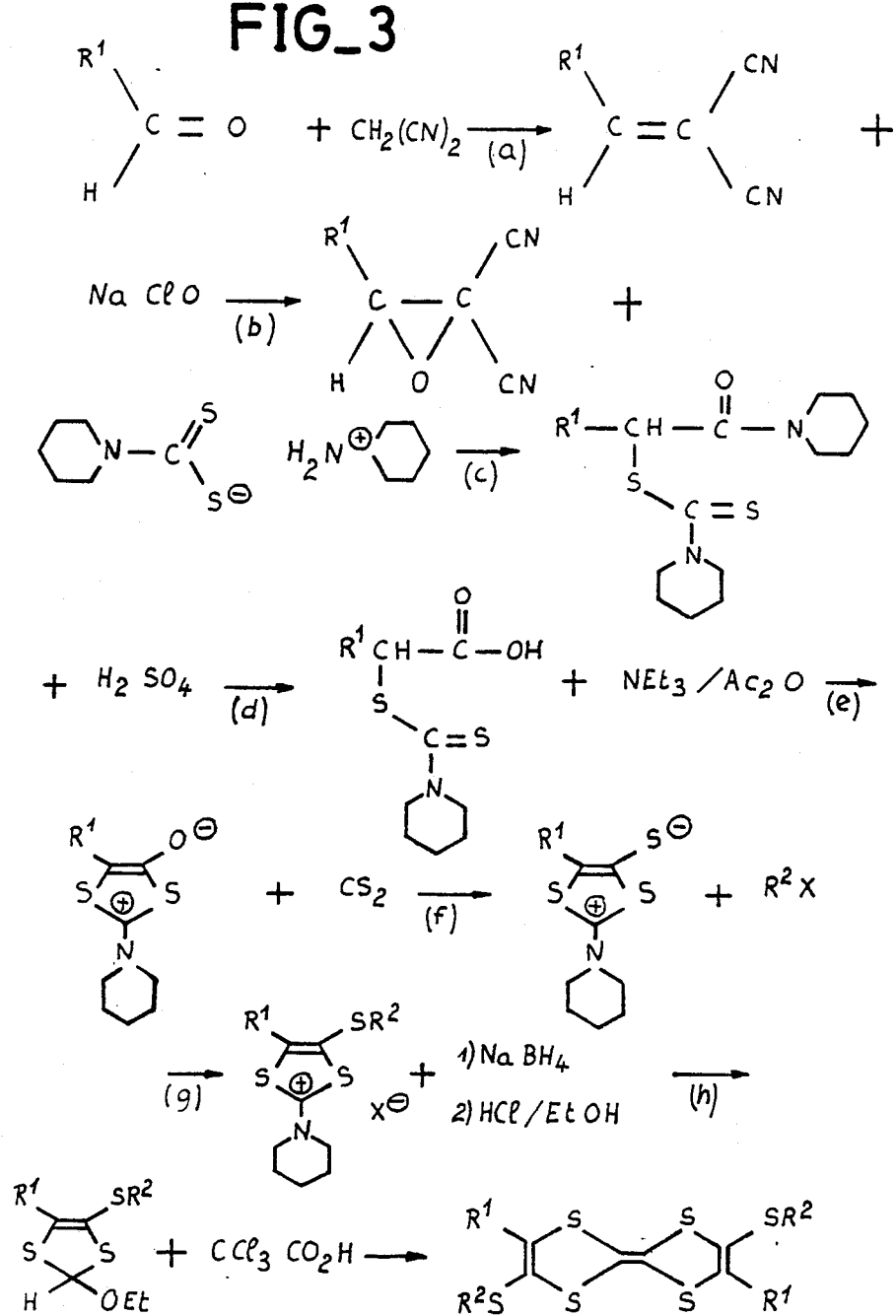

ORGANIC COMPOUNDS OF THE TETRATHIAFLUVALENE TYPE WHICH CAN BE USED TO MAKE LANGMUIR-BLODGETT CONDUCTING FILMS AND METHOD FOR THEIR MANUFACTURE

BACKGROUND OF THE INVENTION

1. Field of the Invention

The present invention pertains to organic compounds of the tetrathiafulvalene type which can be used to make Langmuir-Blodgett conducting films.

The Langmuir-Blodgett method makes it possible to obtain very thin (10 to 40 angstroms) organized monolayers on the surface of a liquid, to transfer these monolayers and to superimpose them on a substrate. The possibilities for the application of these films are derived from the following characteristics: simplicity of the preparation method, very high precision of thicknesses obtained (a few angstroms), orientation of the molecules and adjustable physical properties.

2. Description of the Prior Art

Langmuir-Blodgett films are obtained from amphiphilic molecules. These molecules are elongated and have a hydrophilic group at one end and a hydrophobic group at their other end. The simplest amphiphilic molecules are the fatty acids $CH_3—(CH_2)_n—COOH$ which consist of a hydrophilic polar head $—COOH$ and a hydrophobic aliphatic chain $CH_3—(CH_2)_n—$. Behenic acid $CH_3—(CH_2)_{20}—COOH$ is one of the most frequently used molecules.

The very small thickness of these films makes them especially valuable in micro-electronics. It has therefore, been sought to make them conduct electricity. EP No. 193 362 describes conducting films of this type made with tetracyanoquinodimethane (TCNQ) suitably substituted so that it can be deposited in the form of a Langmuir-Blodgett film.

Another type of conductivity would be of greater value in electronics. This is anisotropic conductivity, especially when the anisotropism is such that the conduction takes place in the direction of the plane of the film while the insulation is provided in a direction perpendicular to this plane.

Organic materials having a conduction anisotropism are already known. Tetrathiafulvalenes (TTF) are electron donor organic compounds which can give rise to the formation of complex compounds through the transfer of charges with electron acceptors. Compounds of this type, known as organic metals, have the remarkable property of conducting electrical current in a preferred direction. In view of the value of these compounds, especially in electronics, a great many works have been devoted to studying their synthesis and their properties (M. Narita, C. U. Pittman Jr., Synthesis 1976, p. 489; J. B. Torrance, Account Chemical Research 1979, No. 12, p. 79, F. Wudl, Account Chemical Research 1984, No. 17, p. 227). However, these molecules are not amphiphilic and, therefore, cannot lead to the formation of Langmuir-Blodgett films. To date, no method is known for the preparation of amphiphilic TTF molecules.

In order to cope with this problem, the invention proposes new molecules of tetrathiafulvalene which are disubstituted so as to be made amphiphilic. It is thus possible to obtain Langmuir-Blodgett thin films which become conductive when they are doped by electron acceptors (iodine, bromine, arsenic pentafluoride, etc.). Furthermore, the layered structure of these films results in a conductivity anisotropism: they are conductive in the directions of the plane of the film and insulating in the direction perpendicular to this plane.

SUMMARY OF THE INVENTION

An object of the invention, therefore, is an organic compound of the tetrathiafulvalene type, which is made amphiphilic by substitution of radicals, the compound having the following formulae

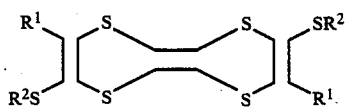

Or

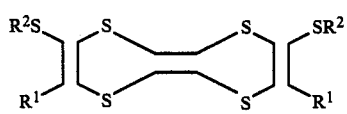

with $R^1$ and $R^2$ meeting one of the following conditions:

$R^1$ is a hydrophilic group and $R^2$ is a hydrophobic group, $R^1$ is a hydrophobic group and $R^2$ is a hydrophilic group, $R^1$ is an aromatic group and $R^2$ is a group having a long carbon-containing chain with a hydrophobic nature and a hydrophilic end.

Another object of the invention is a method for the manufacture of this organic compound.

Yet another object of the invention is a Langmuir-Blodgett film made with the above organic compound, the film being made conductive by doping, for example by using electron acceptor chemical elements.

BRIEF DESCRIPTION OF THE DRAWINGS

The invention will be better understood and other of its advantages will emerge from the following description, given as a non-exhaustive example, and the appended drawings, of which:

FIGS. 1 and 2 represent two possible configurations for the molecules according to the invention;

FIG. 3 illustrates the general method for the synthesis of molecules according to the invention;

FIG. 4 represents an TTF molecule according to the invention.

DESCRIPTION OF PREFERRED EMBODIMENTS

The new molecules according to the invention have the general chemical formulae shown in FIGS. 1 (trans-form) and 2 (cis-form). In either of these formulae, it is possible to have the following:

$R^1$ represents a hydrophilic group and $R^2$ represents a hydrophobic group;

$R^1$ represents a hydrophobic group and $R^2$ represents a hydrophilic group;

$R^1$ represents an aromatic group and $R^2$ has a long carbon-containing chain with a hydrophobic nature and a hydrophilic end.

The method used to prepare these new TTFs makes it possible to substitute them both by hydrophilic groups an by hydrophobic groups. This results in amphiphilic molecules which are very well suited to the making of Langmuir-Blodgett films.

GENERAL METHOD OF SYNTHESIS

The general method of synthesis is shown in FIG. 3. It comprises the following steps:

Step (a): the preparation of an ethylenic compound by the action of malonitrile $CH_2(CN)_2$ on an aldehyde comprising the radical $R^1$, Step (b): the preparation of an epoxide by the action of sodium hypochlorite on the product obtained in the step (a), Step (c): the preparation of an amide by action of piperidinium dithiocarbamate on the product obtained in the step (b), Step (d): the transformation of the product obtained in the step (c) into carboxylic acid, preferably by the action of sulphuric acid.

Steps (e) and (f): the step (e) does not have to be separate; the acid obtained in the step (d) is subjected to the action of a mixture consisting of acetic anhydride, triethylamine and carbon disulphide to obtain mesoionic dithiole.

Step (g): the preparation of a dithiolium salt by the action of a halogenic derivate comprising the radical $R^2$ and a halogen X on the product obtained at the end of the step (f)

Step (h): the preparation of ethoxydithiole by the action of sodium hydroboride and hydrochloric acid on the product obtained at the end of the step (g), Step (i): preparation of the TTF compound according to the invention by the action of trichloroacetic acid $CCl_3CO_2H$ on the product obtained in the step (h).

EXAMPLE OF THE SYNTHESIS OF A MOLECULE

By way of example, we shall describe more precisely the preparation of a particular molecule for which the radicals $R^1$ and $R^2$ are the following:

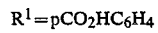

$R^1 = pCO_2HC_6H_4$

$R^2 = (CH_2)_{17}CH_3$

Step (a)

A suspension consisting of 0.1 mole of malonitrile, 200 cm$^3$ of dioxan and 0.1 mole of 4-carboxybenzaldehyde is cooled in ice then 7 cm$^3$ of piperidine is added to it. After been shaken for 40 minutes, the mixture is diluted with 100 m$^3$ of iced water, then acidified with 6N hydrochloric acid. Then an extraction with ether is done. After the evaporation of the solvent, the ethylenic compound is obtained quantitatively.

Step (b)

To 10 grams of ethylenic compound obtained at the end of the step (a), in suspension in 120 cm$^3$ of acetonitrile, 120 cm$^3$ of 2.3N sodium hypochlorite is added, while shaking the mixture and while keeping the pH in the region of 6 by adding 2N sulphuric acid. After 10 minutes, 200 cm$^3$ of iced water is added and the medium is extracted by ether. The evaporation of ether leads to epoxide with a melting point of 214° C.

Step (c)

To a suspension of $6 \times 10^{-3}$ mole of piperidinium dithiocarbamate in 15 cm$^3$ of dry tetrahydrofuran, $7 \times 10^{-3}$ mole of epoxide obtained at the end of the step (b), dissolved in 15 cm$^3$ of dry tetrahydrofuran are added drop by drop, while shaking the mixture, under a nitrogen atmosphere. After 15 hours at ambient temperature, the medium is acidified by 6N hydrochloric acid. The precipitate formed is washed with water and dried. The amide obtained has a melting point of 208° C.

Step (d)

5.5 g. of amide obtained earlier are put into solution in 60 cm$^3$ of sulphuric acid. After two hours at ambient temperature, the solution is diluted with ice until the complete precipitation of the desired acid which has a melting point of 205° C.

Step (e) and (f)

These steps lead to the synthesis of mesoionic dithiole. This compound can be obtained directly from the acid obtained at the end of the step (d) without its being necessary to isolate the product resulting from the step (e).

A mixture consisting of 1 g. of the acid obtained previously, 5 cm$^3$ of acetic anhydride, 2 cm$^3$ of triethylamine and 5 cm$^3$ of carbon disulphide is brought to boiling point for 1 hour. The solution is then cooled and the precipitate obtained is centrifuged, washed with ether and re-crystallized in acetonitrile. The melting point of the mesoionic dithiole obtained is greater than 260° C.

Step (g)

$2 \times 10^{-3}$ mole of the mesoionic derivate obtained previously, in suspension in 30 cm$^3$ of dry acetone, is added to $8 \times 10^{-3}$ moles of halogenic derivate $Br(CH_2)_{17}CH_3$, and the suspension is heated in a reflux condenser for 16 hours. After the evaporation of the solvent, dithiolium salt is obtained and can be used directly for the next step.

Step (h)

The dithiolium salt obtained in the previous step is partially dissolved in 20 cm$^3$ of ethanol. To the suspension, cooled in an ice bath, 100 mg of sodium hydroboride is added while shaking the mixture. After 10 minutes, 1 cm$^3$ of 12N hydrochloric acid is added and, after 30 minutes at ambient temperature, the medium is diluted with 60 cm$^3$ of water, then extracted under ether. After the evaporation of the solvent, the product obtained (ethoxydithiole) is isolated in the form of a yellow solid with a melting point of 89° C.

Step (i)

$2 \times 10^{-3}$ mole of the dry ethoxydithiole obtained in the previous step is heated in a reflux condenser for 1 hour in 70 cm$^3$ of dry benzene in the presence of 500 mg of trichloroacetic acid. After cooling, the solution is washed with water until the neutralization of the washing water, and then evaporated. The TTF is obtained in the form of a red solid, washed with ether and then re-crystallized in ethyl acetate. The melting point of the product obtained ranges between 140° C. and 150° C. The FIG. 4 represents a molecule of the TTF obtained.

The general method of synthesis provides for the making of molecules according to the invention. These molecules are, among others, those for which certain characteristics are summarized in tables 1 and 2 placed at the end of the description. The table 1 pertains to mesoionic dithioles obtained at the end of the step (f) and according to certain radicals $R^1$. The table 2 pertains to TTF molecules for certain compounds of the radicals $R^1$ and $R^2$. These two tables indicate the value of the melting points F of the various products as well as the data pertaining to the NMR characteristics (protons). For the table 1, the solvent used for the characterization is deuterated chloroform. For table 2, it is either deuterated pyridine or deuterated chloroform.

It must be noted that when $R^1 = pCO_2HC_6H_4$ (as is the case in the example described in greater detail above), this radical $R^1$ acquires, during the step (e), a group CO which it loses during the step (h). This is why the first radical $R^1$ of table 1 appears in the form $pCH_3COOCOC_6H_4$.

The TTF molecule with a trans- or cis-form, the synthesis of which is described above, is wholly suited to the formation of a monolayer film on the surface of water. This monolayer film can then be transferred to a substrate in order to prepare a Langmuir-Blodgett film. An example of the manufacture of a film of this type is described below.

$10^{-3}M$ of the TTF molecules are put into solution in chloroform. This solution is then deposited on the surface of a container of water in which calcium chloride $10^{-3}M$ is dissolved. The TTF molecules then form a monolayer which can be compressed to obtain a monolayer film which is compact and stable on the surface of the water. This film is then transferred and superimposed on a substrate.

Several prior art methods may be used to make the film conductive. For example, electron acceptor chemical elements such as iodine, bromine, arsenic pentafluoride, TCNQ, etc. may be made to react on this film. Again, these layers may be doped by dissolving the electron acceptor elements in the water of the container, thus forming a conductive monolayer directly on the surface of the water. It is also possible to prepare the complex compound formed by TTF and electron acceptor chemical elements in solution in chloroform, and thus form a conductive monolayer directly on the surface of the water.

At the end of the operation a Langmuir-Blodgett film is obtained, the thickness of which may comprise one or more layers, each layer being about 30 angstroms thick. This film conducts electricity in the plane of the film and is insulating in a direction perpendicular to the said plane.

TABLE 1

| $R^1$ | F (°C.) | RMN |
|---|---|---|
| $pCH_3COOCOC_6H_4$ | >260 | 1.82 (m, 6 H); 2.42 (s, 3 H) 3.62 (m, 4 H); 8.13 (m, 4 H) |
| $CH_3(CH_2)_{10}$ | 115 | 0.87 (t, 3 H); 1.25 (m, 18 H) 1.78 (m, 6 H); 2.70 (t, 2 H) 3.67 (m, 4 H) |
| $pClC_6H_4$ | 266 | 1.60 (m, 6 H); 3.60 (m, 4 H) 7.70 (m, 4 H) |

TABLE 2

| $R^1$ | $R^2$ | F (°C.) | RMN |
|---|---|---|---|
| $pCO_2HC_6H_4$ | $(CH_2)_{17}CH_3$ | 140–150 | (deuterated pyridine) 0.94 (t, 6 H); 1.36 (m, 64 H) 2.92 (t, 4 H); 8.15 (m, 8 H) |
| $pClC_6H_4$ | $(CH_2)_{10}CO_2H$ | 138–140 | (deuterated chloroform) 1.23 (m, 32 H); 2.37 (t, 4 H) 2.62 (t, 4 H); 7.40 (m, 8 H) |
| $(CH_2)_{10}CH_3$ | $CH_2CO_2H$ | 90–95 | (deuterated pyridine) 0.86 (t, 6 H); 1.26 (m, 36 H) 2.75 (t, 4 H); 3.87 (s, 4 H) |
| $(CH_2)_{10}CH_3$ | $(CH_2)_{10}CO_2H$ | 108–112 | (deuterated pyridine) 0.90 (t, 6 H); 1.30 (m, 74 H) 2.65 (m, 12 H) |

What is claimed is:

1. An organic compound having the formula:

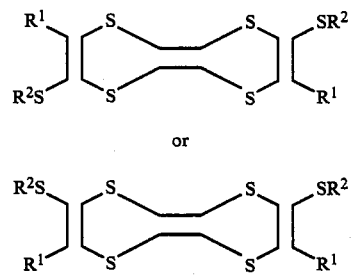

or which is made amphiphilic by substitution of radicals, wherein $R^1$ is $p—CO_2HC_6H_4$ and $R^2$ is $(CH_2)_{17}CH_3$; or $R^1$ is $p—ClC_6H_4$ and $R^2$ is $(CH_2)_{10}CO_2H$; or $R^1$ is $(CH_2)_{10}CH_3$ and $R^2$ is $CH_2CO_2H$; or $R^1$ is $(CH_2)_{10}CH_3$ and $R^2$ is $(CH_2)_{10}CO_2H$.

2. The compound according to claim 1 wherein $R^1$ is the group $pCO_2HC_6H_4$ and $R^2$ is the group $(CH_2)_{17}CH_3$.

3. The compound according to claim 1 wherein $R_1$ is the group $pClC_6H_4$ and $R^2$ the group $(CH_2)_{10}CO_2H$.

4. The compound according to claim 1 wherein $R_1$ is the group $(CH_2)_{10}CH_3$ and $R^2$ the group $CH_2CO_2H$.

5. The compound according to claim 1 wherein $R^1$ is the group $(CH_2)_{10}CH_3$ and $R^2$ is the group $(CH_2)_{10}CO_2H$.

* * * * *